(12) United States Patent
Soini et al.

(10) Patent No.: US 10,295,465 B2
(45) Date of Patent: May 21, 2019

(54) USE OF TWO-PHOTON EXCITED FLUORESCENCE IN ASSAYS OF CLINICAL CHEMISTRY ANALYTES

(75) Inventors: Erkki Soini, Kirjala (FI); Aloksi Soini, Lieto (FI); Juhani Soini, Turku (FI); Niko Meltola, Piispanristi (FI)

(73) Assignee: Arctic Diagnostics Oy, Turku (FI)

(*) Notice: Subject to any disclaimer, the term of this patent is extended or adjusted under 35 U.S.C. 154(b) by 2639 days.

(21) Appl. No.: 10/588,861

(22) PCT Filed: Feb. 11, 2005

(86) PCT No.: PCT/FI2005/050028
§ 371 (c)(1),
(2), (4) Date: May 3, 2007

(87) PCT Pub. No.: WO2005/078438
PCT Pub. Date: Aug. 25, 2005

(65) Prior Publication Data
US 2007/0287186 A1    Dec. 13, 2007

Related U.S. Application Data

(60) Provisional application No. 60/544,197, filed on Feb. 13, 2004.

(30) Foreign Application Priority Data

Feb. 13, 2004 (FI) .................................. 20040236

(51) Int. Cl.
*G01N 33/72* (2006.01)
*G01N 21/64* (2006.01)
(Continued)

(52) U.S. Cl.
CPC ....... *G01N 21/6428* (2013.01); *G01N 33/582* (2013.01); *Y10T 436/16* (2015.01);
(Continued)

(58) Field of Classification Search
CPC .............. G01N 21/6428; G01N 33/582; Y10T 436/19; Y10T 436/20; Y10T 436/175383; Y10T 436/16; Y10T 436/204998
See application file for complete search history.

(56) References Cited

U.S. PATENT DOCUMENTS 5,815,262 A   9/1998  Schrof et al. ................. 356/318
6,342,397 B1* 1/2002  Soini ................... G01N 21/6428
                                                              250/298

(Continued)

FOREIGN PATENT DOCUMENTS

WO    WO 01/54813     8/2001
WO    WO 02/079765   10/2002
WO    WO 03/005030    1/2003

OTHER PUBLICATIONS

WIPO translation of WO/2002/008732 ( EP2001/008328), Jan. 1, 2002.*

(Continued)

*Primary Examiner* — Rebecca M Fritchman
(74) *Attorney, Agent, or Firm* — James C. Lydon

(57) ABSTRACT

The invention relates to an in vitro diagnostic method for quantification of a clinical chemistry analyte from a clinical sample wherein the clinical chemistry analyte undergoes a chemical reaction or reactions with a reagent or reagents in one or several steps, or in a reaction sequence, or catalyzes a chemical reaction, or reactions, or a reaction in a reaction sequence of a reagent or reagents, in one or several steps, in a reaction system. The reaction or reactions or reaction sequence result in a change of a measurable property of a compound or compounds of said reaction or reactions or reaction sequence. Characteristic for the method is that said chemical reaction or reactions or reaction sequence results in formation of a two-photon fluorescent compound, or a change in two-photon fluorescence properties of the reaction system comprising at least one two-photon fluorescent compound, and the analyte is quantified by exciting said two- (Continued)

photon fluorescent compound or compounds and measuring two-photon exited fluorescence, and relating said measured fluorescence to method standardization data based on measurements obtained from reference material of said analyte. The present invention also relates to use of a fluorometric device employing two-photon fluorescence excitation for quantification of a clinical chemistry analytes. The present invention further relates to a system for quantification of clinical chemistry analytes from samples containing the analyte. Characteristic for the system is that it comprises a fluorometric device employing two-photon excited fluorescence for quantifying one or several clinical chemistry analytes, and a data processing unit with software for dedicated data reduction for quantification of the analyte or analytes using said fluorometric device. The present invention further relates to a software product for the system.

7 Claims, 7 Drawing Sheets

(51) Int. Cl.
*G01N 33/58* (2006.01)
*G01N 21/76* (2006.01)

(52) U.S. Cl.
CPC .... *Y10T 436/175383* (2015.01); *Y10T 436/19* (2015.01); *Y10T 436/20* (2015.01); *Y10T 436/204998* (2015.01)

(56) References Cited

U.S. PATENT DOCUMENTS

| | | | |
|---|---|---|---|
| 6,344,653 B1 | 2/2002 | Webb et al. | 250/458.1 |
| 6,537,829 B1* | 3/2003 | Zarling | B82Y 15/00 |
| | | | 250/458.1 |
| 2004/0022684 A1* | 2/2004 | Heinze | B82Y 10/00 |
| | | | 422/82.08 |
| 2004/0052489 A1 | 3/2004 | Duveneck et al. | 385/130 |

OTHER PUBLICATIONS

Heinze et al. (Simultaneous two-photon excitation of distinct labels for dual-color fluorescence cross-correlation analysis, PNAS, vol. 97, pp. 10377-10382 (2000)).*

* cited by examiner

USE OF TWO-PHOTON EXCITED FLUORESCENCE IN ASSAYS OF CLINICAL CHEMISTRY ANALYTES

This application is the U.S. National Stage of International Application No. PCT/FI2005/050028, filed Feb. 11, 2005, which claims benefit of U.S. Provisional Application No. 60/544,197, filed Feb. 13, 2004, and Finnish Application No. 20040236, filed Feb. 13, 2004.

FIELD OF THE INVENTION

Present invention relates to clinical chemistry and to the use of two-photon excited fluorescence as detection principle for measurement of clinical chemistry analytes.

BACKGROUND OF THE INVENTION

The publications and other materials used herein to illustrate the background of the invention, and in particular, cases to provide additional details respecting the practice, are incorporated by reference.

Clinical Chemistry Assays

With clinical chemistry analytes we mean in this context metabolites or other components of serum that are commonly measured in the clinical chemistry practice. Examples of such analytes are as follows: Glucose, total cholesterol, HDL cholesterol, LDL cholesterol, triglycerides, bilirubin, creatinine, total proteins, iron, magnesium, urea, uric acid, ASAT, ALAT, amylase, LDH, GT, alkaline phosphatase, lipase and creatine kinase. In this context, clinical chemistry analytes do not include analytes, which are measured with bioaffinity binding assay techniques, such as immunometric assay, competitive binding assay, antigen bridging assay or agglutination assay methods (The Immunoassay Handbook, 1994, David Wild, Editor, ISBN 0-333-51179-4).

Most often clinical chemistry analytes are assayed with methods based on photometric detection. The assay protocols include addition of one or several reagents to a sample (e.g. blood, plasma, serum, urine, or other body fluid, diluted or undiluted in an appropriate aqueous or non-aqueous diluent) and incubation at constant condition in one or several occasions after or in-between the reagent additions. Finally, absorption of the assay mixture is measured at one or several wavelengths ranges, followed by calculation of the analyte concentration by aid of standard curves and calibrators. Many of the clinical chemistry assays are based on enzyme-catalyzed reaction where the enzyme acts either as the analyte or as an analyte specific reaction catalyst. As a result of the enzyme catalyzed reaction, a change in the structure of a substrate molecule takes place leading to a change in the absorption properties of the substrate. A change in the photometry reading, at an appropriate wavelength, is proportional to the concentration of the analyte in the sample. In case the analyte acts as a substrate and the enzyme acts as a reagent, the reaction can be run in completion and measured end-point, whereas when the enzyme acts as the analyte, the assay reaction is run under strictly controlled conditions, and measured kinetically. In this context, the term kinetic measurement means that the sample is either measured at certain fixed time point (or time points) or, alternatively, if the kinetics of the reaction is well characterized and modeled mathematically, the reaction can be measured at any precise time point (or time points) followed by calculation of the final enzyme activity (concentration in activity units) using the kinetic equations determined before-hand for this particular application. The assay routines and methodology, which are in common use in the clinical chemistry practice, are well described in textbooks and in the literature (Tiez Textbook of Clinical Chemistry, Ed. C. Burtis and E. Ashwood, W. B. Saunders Company). Another type of clinical chemistry assays is those, which do not include enzyme catalysis, but are of pure chemical basis (non-enzymatic reactions). Such analytes include, for example, assay of bilirubin using the diazoreagent, assay of serum protein using the biuret reaction and assay of albumin using BCG (bromocresol green) reagent (Tiez Textbook of Clinical Chemistry, p. 702). These reactions result in formation of a colorful end-product, the concentration of which is measured by photometry using an appropriate wavelength range. The most typical configuration of a photometry analyzer in the clinical chemistry practice includes a single illumination beam and disposable photometry cuvettes. This means, that any variation in the optical length of the disposable cuvettes or in the optical quality of the cuvette walls causes imprecision in the final assay result. Due to this property of photometry, and on the other hand, due to rather strict precision requirements of clinical chemistry assays, the quality requirements focused on the disposable cuvette are very demanding. For this reason the cuvettes for clinical chemistry assays are and remain expensive. In practice, the cuvette is the major constituent of the cost of the photometric clinical chemistry assays.

Some of the clinical chemistry analytes have also been determined by methods based on fluorescence detection (one-photon excited fluorescence). These assays have been realized by replacing the chromogenic substrate (or reagent) used in photometric methods, with a fluorogenic substrate (or reagent). Consequently, the fluorescence signal obtained from the assay mixture is proportional to the concentration of the analyte. Examples of such assays are, to name some, the assay of glucose using glucose oxidase, peroxidase and Amplex Red™ (fluorogenic substrate, trade mark of Molecular Probes, cat no A-12222) as reagents, and the assay of creatinine using creatininase, creatinase, sarcosine oxidase, peroxidase and Amplex Red as reagents. Another example, is the assay of amylase using fluorophore labeled starch as reagent (or other starch analogue such as amylopectine, or an appropriate synthetic reagent such as α-1,4-oligosaccharide), where the labeled starch is working as substrate for the enzyme providing increase of fluorescence as the amylase enzyme digests the polymer reagent (or oligomer)(Fluorescence Microplate Assays, Molecular Probes, Seventh edition, 2002, p. 51). Another example of fluorometric assay methods is the assay of alkaline phosphatase using a phosphate derivatized fluorescein as fluorogenic substrate (Handbook of fluorescent probes and research products, 9th Ed., p. 420, Molecular Probes, Eugene, Oreg., USA, 2002). This assay is based on increase of fluorescence intensity as the analyte hydrolyses the fluorogenic substrate. The fluorescence based assays are, however, mainly used in research laboratories, whereas their use in the clinical chemistry practice is very limited. In general, fluorescence based methods offer orders of magnitudes higher sensitivity, and broader dynamic range than the methods based on photometry. In research laboratories, these properties give a clear advantage, but in clinical chemistry applications, this has not been found that advantageous because the requirements for sensitivity or dynamic range of the clinical chemistry assays are most often rather modest. Instead, accuracy, precision and the reagent cost are generally considered more important criteria for the clinical chemistry assays. In terms of these criteria, fluorometry has not, until to date, been found to provide clear enough advantages over photometry as a detection technique in the clinical chemistry practice.

Applications of Fluorescence in Bioaffinity Assays

One-photon excited fluorescence has found various applications in the field of bioanalytics. Applications such as immunoassays, DNA-hybridization assays and receptor binding assays using fluorescence as detection method have been introduced during the last three decades. These assays utilize specific bioaffinity reactions in determination of the analyte in a sample. The amount of analyte can be determined by monitoring the fluorescence signal that depends on the amount of the bound analyte. These assays can also be based on monitoring of the change in the fluorescence properties upon a specific binding reaction. This change in fluorescence property can be either a change in fluorescence intensity, a change in emission wavelength, a change in decay time or in fluorescence polarization.

Immunoassays have been used extensively in clinical diagnostics for determination of certain diseases or physiological condition. Immunoassays can be categorized to two different types of assays, competitive and non-competitive assays. In the competitive method, a labeled antigen (secondary biospecific reagent) competes with the analyte in binding to a limited quantity of antibody (primary biospecific reagent). The concentration of the analyte can be determined from the proportion of the labeled antigen bound to the antibody or from the proportion of the free fraction of the labeled antigen. In a non-competitive method (immunometric method) the analyte is bound to an excess amount of binding antibody (primary biospecific reagent). An excess of labeled antibody (secondary biospecific reagent) binds to another site of the analyte. The amount of analyte can be determined on basis of the fraction of the labeled antibody bound to the analyte. Physical separation of the bound and free fractions is normally necessary before detection unless the detection principle is able to distinguish the signal of the bound fraction from the signal of the free fraction. Thus, the assay methods are divided in to separation assays and separation-free assays, often also called as heterogeneous and homogeneous assays. [Miyai K., Principles and Practice of Immunoassay, (ed. Price C. P. and Newman D. J.) Stockton Press, New York 1991, 246 and Hemmila I. A., Applications of Fluorescence in Immunoassays, (ed. Winefordner J. D.) John Wiley & Sons, New York 1991]. Coated tube technology is commonly used for separation assays, and in such cases the free fraction is separated with repeated steps of washing.

One-photon excited fluorometry provides sensitivity and a dynamic range that are higher and wider than that of photometry. However, the sensitivity is sufficient only for a limited number of analytes. Time-resolved fluorescence, chemiluminescence and electrochemiluminescence techniques provide improved sensitivity if compared to conventional steady state (i.e. prompt) fluorescence. These techniques have gained popularity both in research and diagnostics field and are considered among the most sensitive analytical techniques (Hemmilä and Mukkala, Crit. Rev. Clin. Lab. Sci. 2001).

Two-Photon Excitation

In 1931 Maria Göppert-Mayer [Ann. Phys. 9 (1931) 273] postulated that a molecule can simultaneously absorb two photons. This phenomenon remained for a long time without any practical use until the intensive laser light sources became available. Two-photon excitation is created when, by focusing an intensive light source, the density of photons per unit volume and per unit time becomes high enough for two photons to be simultaneously absorbed by the same chromophore. The absorbed energy is the sum of the energies of the two photons. The probability of two-photon excitation is dependent on the 2nd power of the photon density. The absorption of two photons is thus a non-linear process of the second order. The simultaneous absorption of the two photons by one chromophore yields a chromophore in excited state. This excited state is then relaxed by spontaneous emission of a photon with higher energy than the photons of the illumination. In this context the process that includes two-photon excitation and subsequent radiative relaxation is called two-photon excited fluorescence (TPE). TPE has usually similar emission properties to those of one-photon excited fluorescence of the same chromophore [Xu C. and Webb W. W., J. Opt. Soc. Am. B, 13 (1996) 481]. The excitation spectrum, however, is sometimes broadened and/or hypsochromically shifted if compared to one-photon excitation spectrum. The molecules, which are excitable by simultaneous absorption of two photons and generate excited states and fluorescence emission, are in this context called two-photon fluorescent dyes.

One of the key features of two-photon excitation is that excitation takes place only in a clearly restricted 3-dimensional (3D) vicinity of the focal point. The outcome of this feature is high 3D spatial concentration of the generated fluorescence emission. Due to the non-linear nature of excitation, minimal background fluorescence is generated outside the focal volume, i.e. in the surrounding sample medium and in the optical components. Another key feature of two-photon excitation is that illumination and emission takes place in essentially different wavelength ranges. A consequence of this property is that leakage of scattered illumination light in the detection channel of the fluorescence emission can be easily attenuated by using low-pass filters (attenuation of at least 10 orders of magnitude). Since the excitation volume is very small (in the range of femtoliters, i.e. 10-15 liters), two-photon excitation is most suitable for observation of small sample volumes and structures.

Bioanalytical Applications of Two-Photon Excited Fluorescence

One of the early reports relative to analytical applications of two-photon excitation was published by Sepaniak et al. [Anal. Chem. 49 (1977), 1554]. They discussed the possibility of using two-photon fluorescence excitation for HPLC detection. Low background and simplicity of the system were demonstrated. Lakowicz et al. [J. Biomolec. Screening 4 (1999) 355] have reported the use of multi-photon excitation in high throughput screening applications. They have shown that two-photon-induced fluorescence of fluorescein can be reliably measured in high-density multi-well plates.

Most of the bioanalytical applications of two-photon excited fluorescence that are described in the literature relate to two-photon imaging microscopy [Denk W. et al. U.S. Pat. No. 5,034,613, Denk W. et al., Science 248 (1990) 73]. The use of two-photon fluorescence excitation in laser scanning microscopy provides inherent 3D spatial resolution without the use of pinholes, a necessity in confocal microscopy. With a simple optical design two-photon excitation microscopy provides comparable 3D spatial resolution to that of ordinary one-photon excited confocal microscopy. The development has also lead to industrial manufacture of two-photon laser scanning microscope systems. The disadvantage of the two-photon excitation technology is the need of an expensive laser capable of generating intense ultra short pulses with a high repetition frequency.

The recent development of less expensive laser technology is very encouraging in regard to usefulness of two-photon fluorescence excitation technology in routine bio-analytical applications [Hänninen P. et al., Nat. Biotechnol. 18 (2000) 548; Soini J. T. et al. Single Mol. 1 (2000) 203; Soini J T (2002) Crit. Rev. Sci. Instr., WO 98/25143 and WO 99/63344]. According to WO 98/25143 and WO 99/63344, instead of expensive mode-locked lasers a passively Q-switched diode-pumped microchip lasers can be used for two-photon excitation. These lasers are monolithic, small, simple and low in cost. WO 98/25143 and WO 99/63344 describe the use of two-photon excited fluorescence in detection of bioaffinity assay. This bioaffinity assay technique employs microparticles as a bioaffinity binding solid phase to which a primary biospecific reagent is bound. This bioaffinity assay technique utilizes a biospecific secondary reagent that is labeled with a two-photon fluorescent dye. According to the methods described in WO 98/25143 and WO 99/63344, bioaffinity complexes are formed on the surface of microparticles, and the amount of bioaffinity complexes is quantified by measuring two-photon excited fluorescence from individual microparticles. Thus, this assay technique enables separation-free bioaffinity assays in microvolumes.

The labeled secondary bioaffinity reagent binds on the surface of microparticles either via an analyte molecule to form three component bioaffinity complexes (non-competitive, immunometric method) or it binds directly to the primary biospecific reagent to form two component bioaffinity complexes (competitive binding method). The primary and secondary biospecific reagents are biologically active molecules, such as haptens, biologically active ligands, drugs, peptides, polypeptides, proteins, antibodies, or fragments of antibodies, nucleotides, oligonucleotides or nucleic acids. According to WO 98/25143 and WO 99/63344 a laser with high two-photon excitation efficiency is focused into the reaction suspension and two-photon excited fluorescence is measured from single microparticles when they float through the focal volume of the laser beam. Alternatively the microparticles can be trapped for a period of fluorescence detection with an optical trap, which is brought about with a laser beam. The trapping of microparticles to the focal point of the laser beam is based on optical pressure that is generated onto the microparticle by the illuminating laser. According to WO 98/25143 optical trapping increases the duration of the particle within the focal volume of the laser beam and increases the duty cycle of the fluorescence detection. The scheme of the optical lay-out of a typical fluorometric device with two-photon excitation is shown in FIG. 1 (ArcDia™ TPX Plate Reader). The construction of the device may vary depending on the particular use and application. The most important components, which characterize the design, are as follows:

The laser beam is focused by a microscope objective lens with a numerical aperture minimum from 0.4 to 0.7.

For trapping the microparticles a two dimensional pietzo driven scanner is employed, which is capable to stop the scan action momentarily when a microparticle is found in the vicinity of the focal volume.

The near infrared laser is a pulse laser with pulse length shorter than 10 nanoseconds, pulse repetition frequency higher than 10 kHz and average beam power in the sample in the order of 100 mW, with TEM 00 mode polarized beam output. A typical laser is a passively q-switched microchip Nd:YAG or Nd:LBS laser [Danailov M B & al., Appl. Phys. B 73, 1-6 (2001)]. An alternative laser would be a mode locked Yb-doped fiber laser [Grudinin A B & al., Optics Letters (2003), Vol. 28 Issue 17 Page 1522]

The fluorescence signal in the visible range of the light spectrum is detected by photomultiplier tubes CPM by using single photon counting.

Current Status of In Vitro Diagnostic Testing

The major sectors of in vitro diagnostics (IVD) testing are: clinical chemistry assays, bioaffinity assays, hematology and microbiology. From these four sectors the most frequent are clinical chemistry assays, however, the highest sales value and growth rate are the bioaffinity assays. The other sectors, microbiology and hematology, together represent only ⅙ of IVD sales volume but are necessary for a complete primary diagnosis and care.

In typical laboratory practice of small and medium size hospitals or health centers, three types of analyzers are commonly needed: 1) a blood cell counting device for hematology, 2) an automated analyzer for clinical chemistry and 3) an immunoassay analyzer. Microbiological testing can be typically performed with rapid stick tests, by visualization of the microbial cultures or by immunoassay, thus, no dedicated instruments are needed for reading the test result.

As discussed above an in vitro diagnostic laboratory needs today at least three major analyzers for performing the variety of the assays that are most frequently requested. Such a high number of analyzers binds capital, and are cost-effective only when the sample throughput rate of the laboratory is high enough to keep the stand-by time of the analyzer as small as possible. According to the current trend in the industrialized countries, the health care system is under very critical cost effectiveness analysis. The government paid reimbursement for the heath care costs is in a pressure to be reduced. Under this pressure both the clinical laboratories and the manufacturers of analyzers and the assay kits are forced to cut down the overall cost of operations per assay and be able to run the IVD service more effectively. As a consequence, centralization of the IVD routines in large laboratories has been taking place. This trend, however, is in contradiction to the need of intensive care, emergency care and polyclinic duty, where IVD results from single patient samples are required without delay. The trend of centralization is nor applicable in rural areas where the distances from the doctor's office to the central hospital is long. Thus, besides to the trend of centralization there is increasing need for point-of-care (POC) testing and distributed IVD analyzers.

Trend for Centralization of IVD

This trend leads to installation of high capacity IVD analyzer in central laboratories. The collection of patient samples would take place either locally in remote doctor's offices or health care centers or in the reception of the central IVD laboratory. In the former case, the patient samples would be collected and transported from the distant regions by a courier to the central IVD laboratory while the latter requires transportation of the patients. Obviously, the direct cost per test is in minimum when the assays are performed in batch manner in a central laboratory by using high capacity analyzers. However, the health care organizations usually focus their attention to the direct assay cost and are not able to count the indirect cost of IVD in the whole health care system. A lot of money is used for transportation of the samples or the patients to the central laboratories and little value is given to the (i) waiting time of a patient, (ii) multiple patient visits or to (iii) stand-alone-time of the samples in non-controlled conditions. In very few cases the overall cost structure of IVD services and logistics is taken into account when IVD methodology and devices are chosen by the authority. In addition, variable waiting time of individual patient samples in non-controlled conditions (temperature, day light exposure) inevitably causes changes in the composition of the sample leading to inaccurate assay result and diagnosis.

Point-of-Care Assays

Point-of-care (POC) platforms are designed for testing of single samples and are characterized by limited assay portfolio. Typically, POC assays are employing non-standard assay methods, produce qualitative or semi-quantitative results, they are operated without supervision of clinical chemistry experts and without connections to databases. POC tests are typically based on the use of prefabricated disposable assay supports. Some of them are based on immunochromatography technique, which incorporate a chromatographic medium and test zone with immobilized immuno reagent. The detection can take place visually or, for example, by photometric, fluorometric, surface plasmon resonance or electroluminescence techniques. POC testing is cost effective in small-scale use—1 000-10 000 per year. In larger quantities, exceeding 10 000 tests per year, POC tests become less cost effective due to high price of disposable assay component. POC devices are practical only in cases where qualitative results are required instantly for single patient samples.

Distributed IVD

In contrast to the trend of centralization, a clear increase in the need for distributed IVD service and analyzers is found. With distributed IVD we mean IVD practices using compact multipurpose IVD analyzers, which are distributed in locations where the samples are taken from the patients, such as local doctor's offices or remote health centers. The analyzers are connected to the database of a central laboratory trough the telecommunication network. The analyzers are operated and supervised by clinical chemistry experts in a central laboratory, thus the analyzers function like chemical sensors positioned close to the patient.

The technology for distributed IVD is not yet very well developed. There is not yet any ideal and suitable methodology and instrumentation commercially available, which would allow cost effective assays for distributed IVD. This is one of the main reasons for the current trend of IVD centralization in industrialized countries. An ideal analyzer for distributed IVD would perform all of the most frequently requested assays, including both clinical chemistry assays and sensitive immunoassays, with a single detector. In order to allow cost effective assays, the analyzer for distributed IVD should perform all assays separation-free, in other words, without washing steps. Such separation-free assay format would significantly simplify the liquid handling robotics, thus making the instrument smaller and less expensive to manufacture. The physical size of the analyzer should be suitable for table-top use. The analyzer should allow operations in reduced assays volumes. This together with separation-free format (no washing steps) would save reagents and liquid consumables, thus increasing cost-efficiency of the technique. The operation of the analyzer should not require personnel with clinical laboratory competence. The cost of the analyzer should not be higher than for example the cost of a small-scale clinical chemistry analyzer or an immunology analyzer. The device should incorporate dedicated data reduction software for clinical chemistry applications and for quantification of the assays and should allow connection to the data network for supervision by an expert in the central laboratory. This means that the analyzers could be distributed in remote places where the samples are taken, while the clinical chemistry expertise, administration of the assay results, quality control and maintenance would be centralized. There are not many analyzers or technologies commercially available, which fulfill these requirements. Small-scale clinical chemistry analyzers and immunoassay analyzers are normally available as separate units. Some of the commercial clinical chemistry analyzers perform also immunoassays in separation-free format. These immunoassays, however, are usually employing either turbidimetry or nephelometry detection principles (agglutination assays), which do not allow high sensitivity assays but are limited to analytes of relatively high clinical reference concentration.

In order to cope with assays of analytes with lower reference concentration, some manufacturers have recently developed analyzers, which combine clinical chemistry assays with immunoassays using heterogeneous immunoassay principle. An example of such analyzer is that of Adaltis (Adaltis Italia S.p.A, Bologna, Italy), which performs clinical chemistry assay by photometry and immunoassays by chemiluminescence detection principle. Heterogeneous immunoassay principle, however, does not allow separation-free assays and is therefore not ideal for distributed IVD. As a conclusion, the IVD market is looking for new instrumental technology that fulfills the requirements as discussed above.

One of the most important problems with the photometric methodology is the need for expensive test cuvette. If the analyzer is equipped with re-usable flow-cuvettes, the cost of cuvette per assay is not a problem. Re-usable flow-cuvettes, however, are not commonly used today due to their sensitivity to analyte and reagent carry-over and contamination. Thus, the majority of the commercial clinical chemistry analyzers employ disposable photometric cuvettes. Due to the inherent nature of photometric detection, the assay result is critically dependent on the optical quality of the test cuvette and on the length of the optical path. These quality requirements necessitate very highly skilled manufacturing technology, thus making the production of the cuvettes expensive and the corresponding assays prone to inaccuracy due to cuvette-to-cuvette variation. For this reason the cuvettes for clinical chemistry assays are and remain expensive. In fact, the cuvette is the major constituent of the cost of clinical chemistry assays that are based on photometry detection.

An additional problem encountered with the precision of the photometric assays is related to the sample matrix interferences. Blood serum and plasma are the typical samples where the metabolites are assayed. The sample can however contain interfering matrix components such as bilirubin, hemoglobin from hemolyzed erythrocytes or turbidity due to particulate lipids. All these substances can interfere strongly in photometric measurements unless the sample is heavily diluted before the assay.

A third problem with photometric detection relates to the assay volumes. The analytical sensitivity of photometric detection is dependent on the length of the optical path. The longer the optical path the higher dilution factor can be applied. This improves tolerance to interference by matrix components and accuracy of detection. Typical optical length with the commercial analyzers is from 5 to 8 mm. Depending on the geometry of the cuvette, this length leads to an assay volume of 100-300 microliter. Such a cuvette is not optimal with immunoassays because the reagents cost of immunoassays is typically ten times higher than the cost of clinical chemistry reagents. Consequently, clinical chemistry analyzers with photometric detection are relative large in size and require rather large reagent and diluent volumes. This property increases the cost of the immunoassays and the advantage of low assay volumes cannot be exploited.

As summary from the discussion above, we can conclude that the IVD market is still missing a technology and analyzer, which would allow both conventional clinical chemistry and high sensitivity immunoassays, and which would perform all of the most frequently requested assays with separation-free methodology in micro-volumes. In addition, the methodology should minimize or eliminate the need of liquid handling other than dilution and dispensing the sample. The methodology should perform the assays with high precision by using low-cost disposable cuvettes and without the need of prefabricated coated tubes or other expensive assay component. The analyzer would thus combine the functions of two large clinical analyzers, the clinical chemistry analyzer and the immunoanalyzer, and thus to allow cost effective assays in microvolumes.

OBJECT AND SUMMARY OF THE INVENTION

One object of the present invention is to provide an improved method for quantification of clinical chemistry analytes.

Another object of the present invention is to provide the use of a device for improved quantification of clinical chemistry analytes.

A further object of the present invention is to provide an improved system for quantification of clinical chemistry analytes.

A still further object of the present invention is to provide software for a system for improved quantification of clinical chemistry analytes.

Thus the present invention provides an in vitro diagnostic method for quantification of a clinical chemistry analyte from a clinical sample wherein the clinical chemistry analyte
 a) undergoes a chemical reaction or reactions with a reagent or reagents in one or several steps, or in a reaction sequence, or
 b) catalyses a chemical reaction, or reactions, or a reaction in a reaction sequence of a reagent or reagents, in one or several steps;
in a reaction system, said reaction or reactions or reaction sequence resulting in a change of a measurable property of a compound or compounds of said reaction or reactions or reaction sequence. Characteristic for the method is that
 i) said chemical reaction or reactions or reaction sequence results in
    formation of a two-photon fluorescent compound, or
    a change in two-photon fluorescence properties of the reaction system comprising at least one two-photon fluorescent compound; and
 ii) said analyte is quantified by exciting said two-photon fluorescent compound or compounds and measuring two-photon exited fluorescence, and relating said measured fluorescence to method standardization data based on measurements obtained from reference material of said analyte.

The present invention also provides a use of a fluorometric device employing two-photon fluorescence excitation for in vitro diagnostic quantification of a clinical chemistry analyte or analytes from a clinical sample or samples, wherein said quantification of one or more of said analytes comprises one or more chemical reactions resulting in formation of at least one two-photon fluorescent compound, or a change in two-photon fluorescence properties of the reaction system comprising at least one two-photon fluorescent compound.

The present invention further provides a system for in vitro diagnostic quantification of at least one clinical chemistry analyte from a clinical sample or samples. Characteristic for the system is that it comprises
 a) a fluorometric device employing two-photon excited fluorescence for quantifying one or several clinical chemistry analytes, and
 b) a data processing unit with software for dedicated data reduction for said quantification of said analyte or analytes using said fluorometric device, wherein said quantification of one or more of said analytes comprises one or more chemical reactions resulting in formation of at least one two-photon fluorescent compound, or a change in two-photon fluorescence properties of the reaction system comprising at least one two-photon fluorescent compound.

The present invention still further provides a software product for the system, being characterized in that the software product comprises means for controlling a processing unit of the quantification system to execute or control quantification of the analyte by exciting the two-photon fluorescent compound or compounds, measuring two-photon excited fluorescence, and relating said measured fluorescence to method standardization data based on measurements obtained from reference material of said analyte.

DETAILED DESCRIPTION OF THE INVENTION

Figure 1:
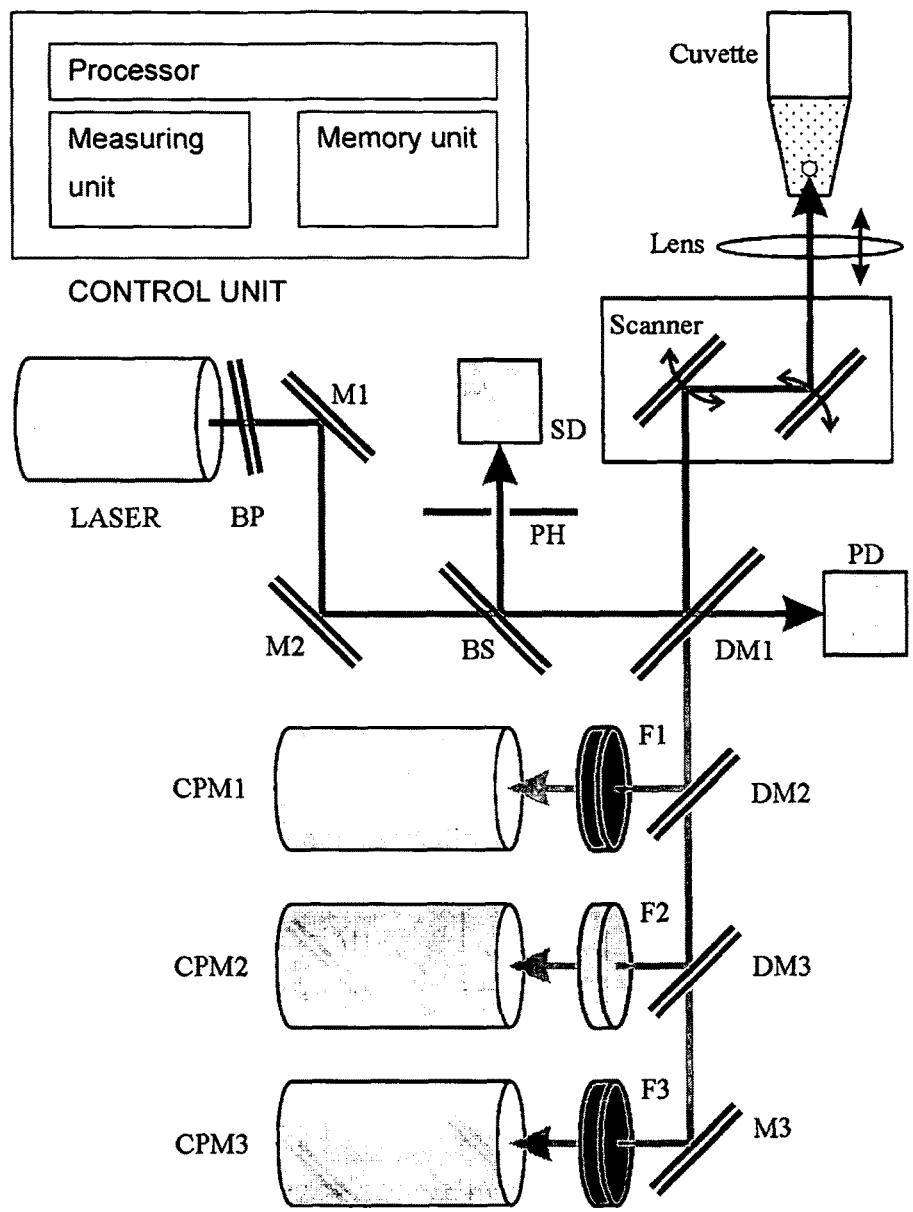
FIG. 1 shows an example of a schematic optical configuration of a fluorometric detector that is based on two-photon excitation and used as measuring device of the present invention.

The invention aims at providing an instrumental technology and methodology, which fulfills the requirements for the distributed IVD analyzer as discussed above. The invention is related to the use of two-photon excited fluorescence (TPE) technology and instrumentation for clinical chemistry assays. The invention is based on the surprising discovery that TPE can be applied not only for sensitive bioaffinity assays (that already has been described in the literature as referred to above) but also for clinical chemistry analytes and allows these two classes of assays to be carried out cost-effectively with the same analyzer. The value of the invention is further increased by the surprising discovery that TPE methodology is exceptionally tolerant to matrix interferences of the sample. The matrix can badly interfere with assays that are based on photometry and conventional one-photon excited fluorometry. TPE-methodology allows immunoassays and clinical chemistry assays to be carried out separation-free, in microvolumes, by using low cost disposable cuvettes (for example standard microtiter plates). Cuvettes with spectrophotometric quality are not needed. The invention has a remarkable reducing effect in the total cost of the clinical chemistry assays, since the cuvette of spectrophotometer quality is the most expensive consumable component of a typical clinical chemistry assay. Thus, TPE methodology allows high sensitivity bioaffinity assays and clinical chemistry assays to be carried out with a single instrument with improved assay performance. The TPE methodology allows also reduction of assay volumes down to 10% from the volumes of current practice. The TPE analyzer can be a table-top analyzer and does not incorporate any liquid handling other than sample dilution and dispensing.

Terms

Terms used in this application can be defined as follows:
One-photon excited fluorescence: Process that includes linear absorption of a single photon by a fluorophore and subsequent radiative relaxation of the excited state.
Two-photon excited fluorescence (TPE): A process where a chromophore is excited by simultaneous absorption of two photons followed by radiative relaxation of the excited state.
Two-photon fluorescent compound: Compound, which can be excited by two-photon excitation, i.e. by simultaneous absorption of two photons, followed by radiative relaxation of the excited state.
Bioaffinity assays: Common name for all bioassays that are based on bioaffinity binding reactions, i.e. a reaction where bioaffinity complexes are formed. These assays include, e.g. immunoassays and nucleic acid hybridization assays. Assays which are based on enzyme catalysed chemical reactions are not bioaffinity binding assays.
Bioaffinity analyte: Common name for analytes which are measured in the clinical practice by bioaffinity assays, using e.g. antibodies or DNA probes as a specific bioaffinity binding probe.
Clinical chemistry assays: Common name for quantitative assays, which incorporate a chemical reaction, measured on regular basis in the clinical chemistry practice, excluding bioaffinity assays.
Clinical chemistry analyte: Common name for analytes, which are measured by means of "clinical chemistry assays".
Fluorogenic substrate: A substrate, which is characterized with either increase or decrease of fluorescence efficiency or change in the emission wavelength, when subjected to an enzyme catalyzed reaction.
3SD: Standard deviation multiplied by a factor of 3. This function is regularly used to determine lowest limit of detection.
Kinetic measurement: The sample is either measured at a certain fixed time point (or certain time points) or, alternatively, if the kinetics of the reaction is well characterized and modeled mathematically, the reaction can be measured at any precise time point (or time points) followed by calculation of the final enzyme activity (concentration in activity units) using the kinetic equation determined before-hand for this particular application.
Assay standardization data: The quantification of the assay is based on the use of appropriate reference material for calibration of the signal response obtained from the detector in appropriate analyte concentration or activity units, and method specific response information provided by the method manufacturer along with the reference material.
A chemical reaction. A reaction where chemical or biochemical compounds are reacted to form new compound or compounds, i.e. a reaction where the chemical primary structure of a compound is changed, or a reaction where a change in the chemical structure takes place in the level of covalent bonding.

Preferable Embodiments of the Invention

The present invention concerns an in vitro diagnostic assay method for measurement of clinical chemistry analytes from a clinical sample (e.g. blood, plasma, serum, urine, or other body fluid) using two-photon excited fluorescence detection. The assay is typically separation-free.

A typical method of the present invention is an in vitro diagnostic method for quantification of a clinical chemistry analyte from a clinical sample wherein the clinical chemistry analyte
  a) undergoes a chemical reaction or reactions with a reagent or reagents, or
  b) catalyses a chemical reaction or reactions of a reagent or reagents;
in a reaction system comprising a reaction or reactions in sequence, said reaction or reactions of said analyte or catalyses resulting in a change of a measurable property of a compound or compounds of said reaction system. Characteristic for the method is that
  i) said chemical reaction or reactions of said analyte or catalyses result in
      formation of a two-photon fluorescent compound, or
      a change in two-photon fluorescence properties of the reaction system comprising at least one two-photon fluorescent compound; and
  ii) said analyte is quantified by exciting said two-photon fluorescent compound or compounds and measuring two-photon exited fluorescence, and relating said measured fluorescence to method standardization data based on measurements obtained from reference material of said analyte.

A preferred method according to the present invention comprises the steps of
  a) bringing the clinical sample comprising the clinical chemistry analyte in contact with a specific assay reagent or reagents;
  b) allowing, in the reaction system, said analyte to undergo a chemical reaction with said reagent or reagents, or allowing said analyte to catalyze a chemical reaction or reactions of said reagent or reagents;
  c) optionally repeating steps a) and b) one or several times;
  d) said reaction or reactions of step or steps b) resulting in formation of a two-photon fluorescent compound, or resulting in a change in two-photon fluorescence properties of said reaction system comprising at least one two-photon fluorescent compound; and
  e) quantifying said analyte by exciting said two-photon fluorescent compound or compounds, measuring two-photon excited fluorescence, and relating said measured fluorescence to method standardization data based on measurements obtained from reference material of said analyte.

The measurement of the fluorescence signal resulting from two-photon fluorescent excitation is measured kinetically or as an end-point signal.

The quantification of the clinical chemistry analyte or analytes can be carried out for several samples as well as for several analytes by repeating the method of the invention for each sample and/or analyte.

The analytes typically include, but are not limited to albumin, total protein, hemoglobin, ammonia, carbonate, bilirubin direct, bilirubin total, calcium, chloride, iron, magnesium, phosphate, cholesterol HDL, cholesterol LDL, cholesterol total, creatinine, fructosamine, glucose, lactate, triglycerides, urea, uric acid, acid phosphatase, alkaline phosphatase, alanine aminotransferase, aspartate aminotransferase, amylase pancreatic, amylase total, cholin esterase, creatine kinase, glutamyl transferase, glutamate dehydrogenase, hydroxybutyrate dehydrogenase, lactate dehydrogenase and lipase.

The fluorometric device employing two-photon fluorescence excitation can, according to the present invention, be used for quantifying one or several clinical chemistry analytes. According to a preferred embodiment of the invention several clinical chemistry analytes, e.g. of those disclosed above, would be quantified using the same fluorometric device employing two-photon fluorescence excitation. Typically at least 2, preferably 5, more preferably 10, even more preferably 20 and most preferably all of the clinical chemistry analytes disclosed above would be consecutively quantified using the same device. The same fluorometric device can, off course, also be used for the quantification of bioaffinity analytes.

The device to be used according to the invention would typically comprise a pulse laser for two-photon fluorescence excitation with a pulse length shorter than 10 nanoseconds, with pulse repetition frequency higher than 10 kHz, with TEM 00 mode polarized beam output, with average beam power in the sample from 20 to 200 mW, preferably 85 to 120 mW and most preferably about 100 mW.

According to the present invention the concentration of an analyte can be quantified by means of two-photon excited fluorescence. The laser is typically focused into the reaction suspension with an objective lens, preferably of high numerical aperture, and the two-photon excited fluorescence is generated in the focal volume (or volumes), collected from the same volume (or volumes) and quantified in one or several wavelengths channels.

According to the present invention, the fluorescence intensity is typically proportional to the concentration or activity of the analyte. The signal response can originate from the analyte as such, or it can originate from a reagent or a reaction product, the concentration of which is either decreasing (reagent) or increasing (reaction product) as a function of the analyte concentration. The signal response can originate also from a reaction product or a product of a reaction sequence or a reaction pathway, where the analyte acts as a reaction component or catalyses at least one of the reactions of the reaction sequence or pathway.

Alternatively, the signal may originate from a fluorescent reagent the emission of which is absorbed (or quenched) by a reaction product, where the formation of said reaction product is proportional to concentration or activity of the analyte.

Some of the assay methods for clinical chemistry analytes originally developed for one-photon excited fluorescence detection are applicable as such or after minor modification in two-photon excited fluorescence detection, whereas some other assay methods are not functional but require major modifications in order to become applicable for two-photon excited fluorescence detection. Whether the method is applicable as such or requires modifications, depends on the chemical properties of the fluorogenic component of the assay method.

The invention also relates to a system and a software product for implementing the quantification method. The system comprises many elements of a prior known quantification system, but a control unit of the system controls the elements to implement the inventive quantification method. The control unit of the system preferably comprises a processor, a memory unit and a measurement unit. The signals from the photo multiplier tubes and possible other sensors are received and measured in the measurement unit. The measurement parameters and the measured data are stored in the memory unit. Software running the processor is also stored in the memory means. The stored software product comprises means for controlling the processor to implement the steps of the inventive quantification method. A preferred software product would comprise means for controlling the processing unit of the quantification system to execute or control any combination of one or more steps of a method according to the invention.

Advantages of the Invention

The present invention describes the use of two-photon excited fluorescence as detection method for clinical chemistry assays and offers the following surprising advantages compared to state-of-the-art techniques:

Advantage 1:

Interference by sample matrix components, such as hemoglobin (hemolyzed serum) or bilirubin (i.e. icteria, bilirubinemia), has found to be significantly smaller with detection by two-photon excited fluorescence than with photometry. In addition, the same advantage is found when two-photon excited fluorescence detection is compared to conventional one-photon excitation fluorometry. This advantage is illustrated by Example 1, which describes a study of the dependence of fluorescence signal intensity on the degree of sample hemolysis. The results of this study are presented graphically in FIG. 2. The figure shows that increase of the degree of hemolysis is accompanied with a decrease of fluorescence signal due to absorption by hemoglobin. In case of one-photon excited fluorometry, the increase in degree of hemolysis from 0 to 1.5 g/liter causes a remarkable decrease in fluorescence signal, from 100% down to 55%, whereas two-photon excited fluorescence is practically unaffected by the same degree of hemolysis. This degree of hemolysis, 1.5 g/liter, is rather moderate and is encountered frequently in a clinical laboratory. This example suggests that clinical chemistry assays with two-photon excited fluorescence detection are exceptionally tolerant to matrix effects, hence, two-photon excited fluorescence detection gives significantly improved accuracy if compared to assays with one-photon excited fluorescence detection. In general, clinical chemistry analytes are characterized with rather narrow clinical reference range. This means that even a small change in the concentration of the analyte may have a remarkable physiological effect or reflect a significant physiological malfunction. For such assays high assay precision and accuracy are required. From instrumental point of view, precision of 2-3% CV (coefficient of variation) can be easily achieved with various detection methods, such as photometry or one-photon fluorometry, but to keep accuracy within the same range causes a major challenge for the current clinical chemistry detection technologies. In fact, many of the clinical chemistry assay methods that are based on photometry or one-photon excitation fluorometry, fail to provide satisfactory accuracy for samples containing an interfering matrix component. Two-photon excited fluorescence detection, as described in this invention, provides remedy for the problem in relation to assay accuracy by being exceptionally tolerant to the effects of matrix components, such as serum hemolysis.

Advantage 2

The second advantage provided by the present invention relates to assay cuvettes. Due to the inherent property of two-photon excited fluorometry, the fluorescence signal intensity is not dependent on the length of the optical path or on the total volume of the cuvette. Instead, TPE fluorescence is generated only in the diffraction limited focal volume, which locates a few hundred micrometers from the back surface of the cuvette window. The fluorescence signal is collected from the same diffraction limited volume through the same objective lens (epi-fluorescence detection). This excitation geometry thus eliminates the need for cuvettes with exact optical length, and allows the use of low-cost disposable assay cuvettes, such as standard microtitration plates. This advantage is illustrated in Example 2, which describes a study of the effect of the optical quality of the assay cuvette window on the precision of the fluorescence measurement. The results (Table 1) show that both microtitration plates, the one with a bottom window of highest quality optical glass and the other with a bottom window of crude plastic foil, provide practically equal signal precision (<2% CV). This example indicates that two-photon excited fluorescence allows the use of standard low-cost cuvettes without compromising in assay precision. Hence, TPE detection technique eliminates the need for expensive cuvettes of high optical quality and allows more cost-effective clinical chemistry assays than the prior art techniques based on photometry or one-photon excited fluorometry.

Advantage 3

The third advantage provided by the present invention relates to the assay volumes. Since TPE signal level is independent of the assay volume, TPE detection allows decreasing of the assay volumes without compromising assay performance. Typical assay volumes in the current clinical chemistry practice are from 100 to 200 µl. With TPE detection the assay volumes could be easily decreased down to 10 µl or even below. Such decrease in the assay volume is naturally accompanied with reduction in reagent consumption and cost. This aspect further strengthens the cost-effectiveness of the TPE detection technique.

Advantage 4:

The fourth advantage provided by the present invention is the higher sensitivity of TPE detection compared to photometry. The lowest limit of detection of the TPE microfluorometer (see Example 1) for a fluorophore in aqueous buffer, such as ArcDia BF560 fluorophore in serum, is around 100 pM ($10^{-10}$ mol/liter), while photometry (path length=5-8 mm) allows detection of the same compound (molar absorption coefficient 80 000 $M^{-1}$ $cm^{-1}$) in concentration of 100 nM ($10^{-7}$ mol/liter). Thus, the difference in the detection limits of the two detection techniques is three orders of magnitude. As far as clinical chemistry assays are concerned, the difference in the detection limits is likely to be smaller, in favor of TPE, due to restrictions arising from reaction kinetics of the assay methods. Because clinical chemistry analytes usually exist in rather high concentrations, the detection limit of photometry is usually very satisfactory. However, the lower detection limit makes an advantage when the sample contains an interfering matrix component. By allowing higher sample dilution, TPE detection technique is less affected by matrix component, thus providing better assay accuracy.

Advantage 5:

The fifth advantage provided by the present invention rises from the fact that clinical chemistry analyzers based on TPE detection enable also high sensitivity immunoassays in separation-free format. A prototype of such an analyzer has now been constructed and its use in high sensitivity bioaffinity assays has been demonstrated. Thus, TPE detection technique allows the design of an analyzer, which would fulfill all the requirements assumed for a successful analyzer for distributed IVD by (i) enabling both clinical chemistry assay and sensitive immunoassays with one and the same detection head, (ii) providing separation-free assay formats, (iii) allowing compact table-top design of the analyzer with simple construction, (iv) allowing assays with reduced reaction volumes, (v) allowing automated operations after manual sample loading (no personnel with special clinical chemistry expertise is needed) (vi) allowing connection to data network for supervision by an expert in the central laboratory, (vii) allowing assays with significantly increased cost-efficiency compared to the state-of-the-art techniques.

DETAILED DESCRIPTION OF FIGURES

FIG. 1 shows an example of a schematic optical configuration of a fluorometric detector that is based on two-photon excitation and used as measuring device of this invention. The construction may vary depending on the particular use and application. Typically the components can be characterized as follows:

Cuvette is a disposable single cuvette or a micro titer plate including an optical bottom window. Various microfluidic chips (lab-on-chip technology) can also be used;

Lens is a microscope objective lens with a numerical aperture of minimum 0.5;

Scanner is a two dimensional pietzo driven scanner capable to stop the scan action momentarily when a microparticle is found in the vicinity of the focal volume;

Laser is a near infrared pulse laser with pulse length shorter than 10 nanoseconds, pulse repetition frequency higher than 10 kHz and average power from 10 to 100 mW, with TEM 00 mode polarized beam output. A typical laser is a passively q-switched microchip Nd:YAG or Nd:LBS laser;

Bp is a band pass filter;

M1 and M2 are beam alignment mirrors;

BS is a beam splitter;

PH is a pinhole;

SD is a scattering light detector operating on the laser output wavelength;

DM1-DM3 are dichroic mirrors;

PD is a photodiode for laser pulse monitoring;

M3 is a mirror;

F1-F2 are interference filters optimized for the emission wavelength of the labeling reagent;

CPM1-CPM3 are photomultiplier tubes for single photon counting; and

Control unit including:
 a measurement unit for receiving the signals from the sensors/photomultiplier tubes
 a processor for controlling the elements of the system in order to implement the inventive quantification method a memory unit for storing measurement results and other assay data and a software program running the processor.

Figure 2:
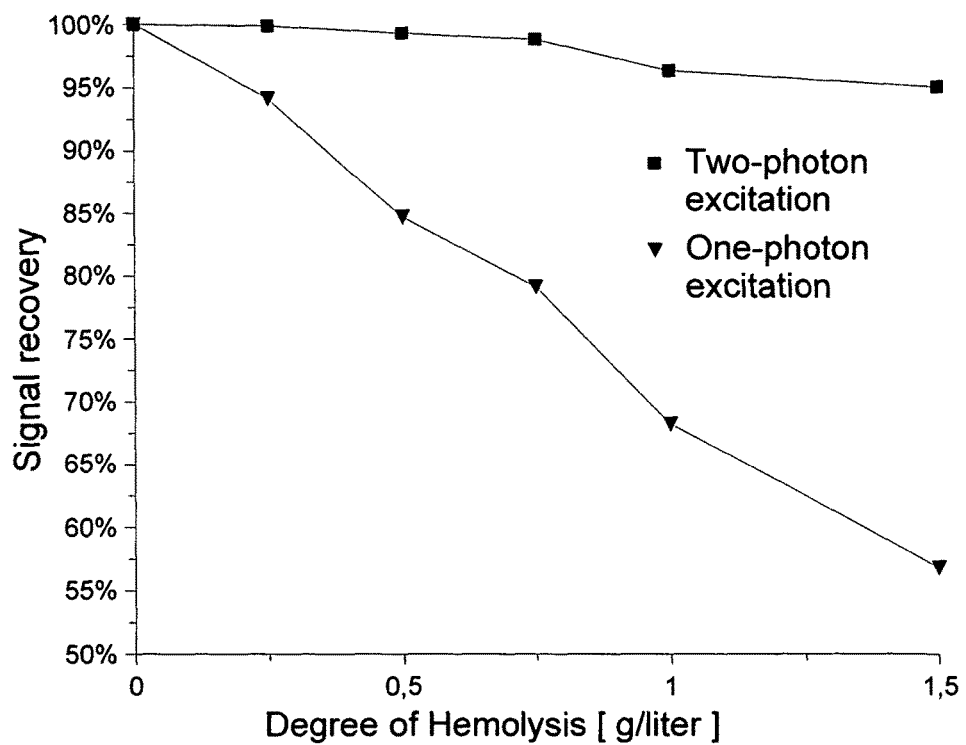
FIG. 2 shows an example of the effect of the degree of hemolysis on signal recovery of one-photon excited fluorescence and two-photon excited fluorescence.

FIG. 2 shows the effect of degree of hemolysis on the signal recovery of one-photon excited fluorescence (triangular) and two-photon excited fluorescence (square).

Figure 3:
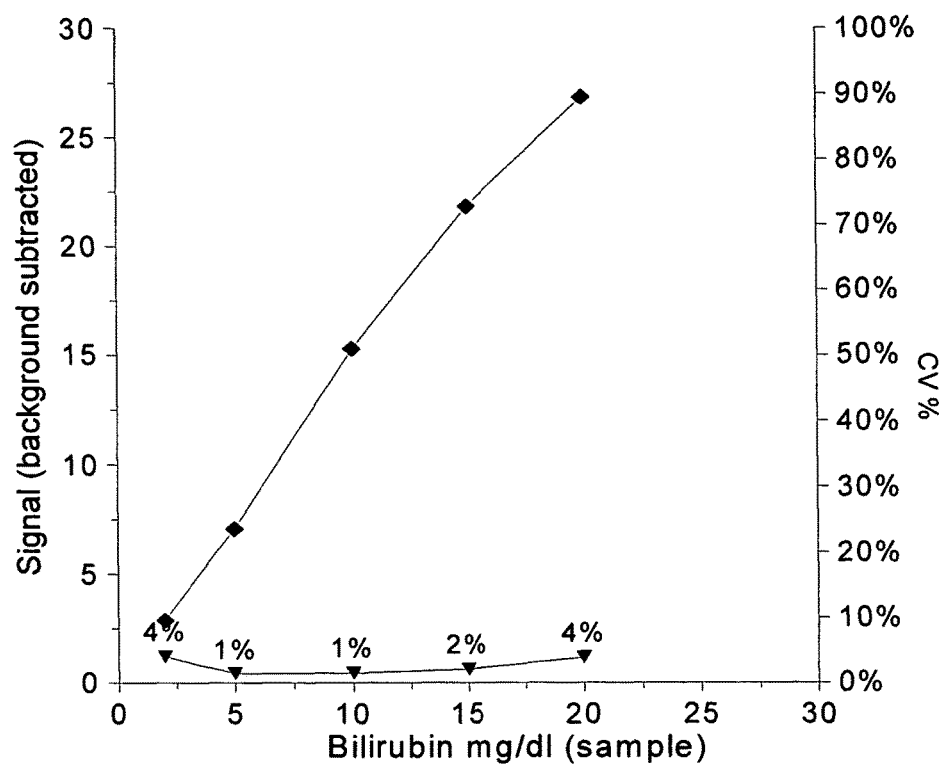
FIG. 3 shows a signal response curve and precision profile of a bilirubin assay.

FIG. 3 shows signal response curve (square) and corresponding precision profile (triangle) of a bilirubin assay method. The precision values are given in coefficient of variation units (CV %).

Figure 4:
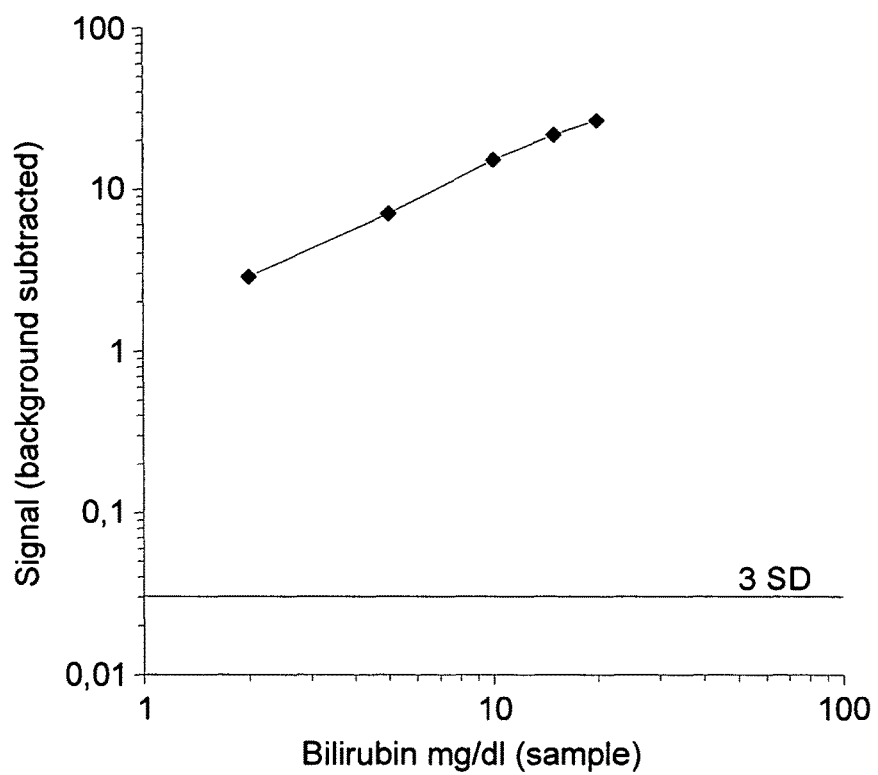
FIG. 4 shows a signal response curve of the bilirubin assay in logarithmic scale.

FIG. 4 shows a signal response curve of the bilirubin assay method in logarithmic scale. 3SD level of the negative control is also presented (horizontal line).

Figure 5:
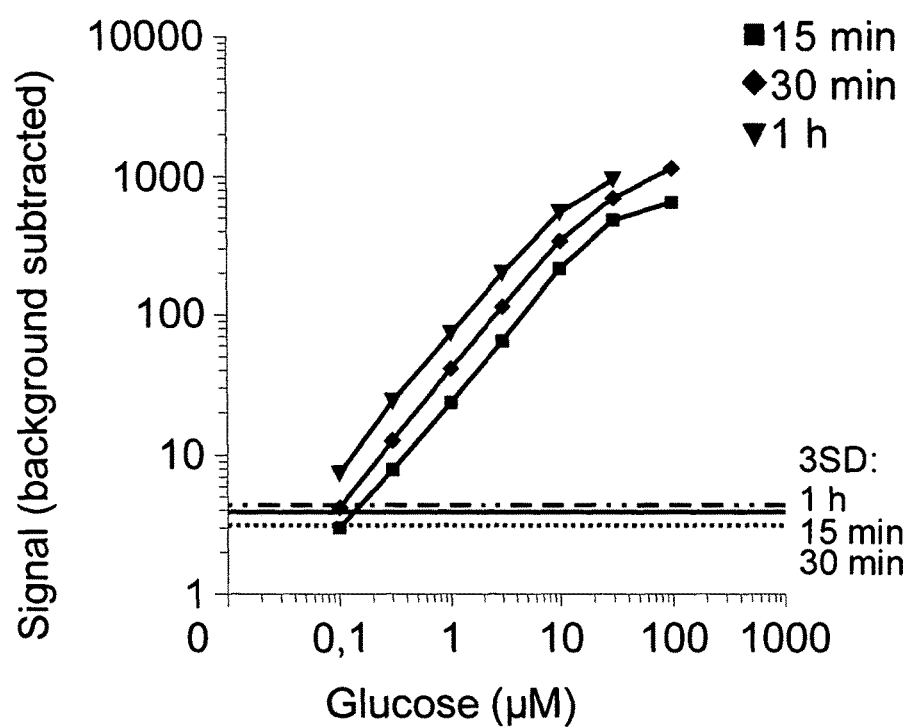
FIG. 5 shows standard curves of a glucose assay with three different incubation times.

FIG. 5 shows standard curves of the glucose assay method with three different incubation times presented. The figure shows also the level of 3SD of the negative control samples.

Figure 6:
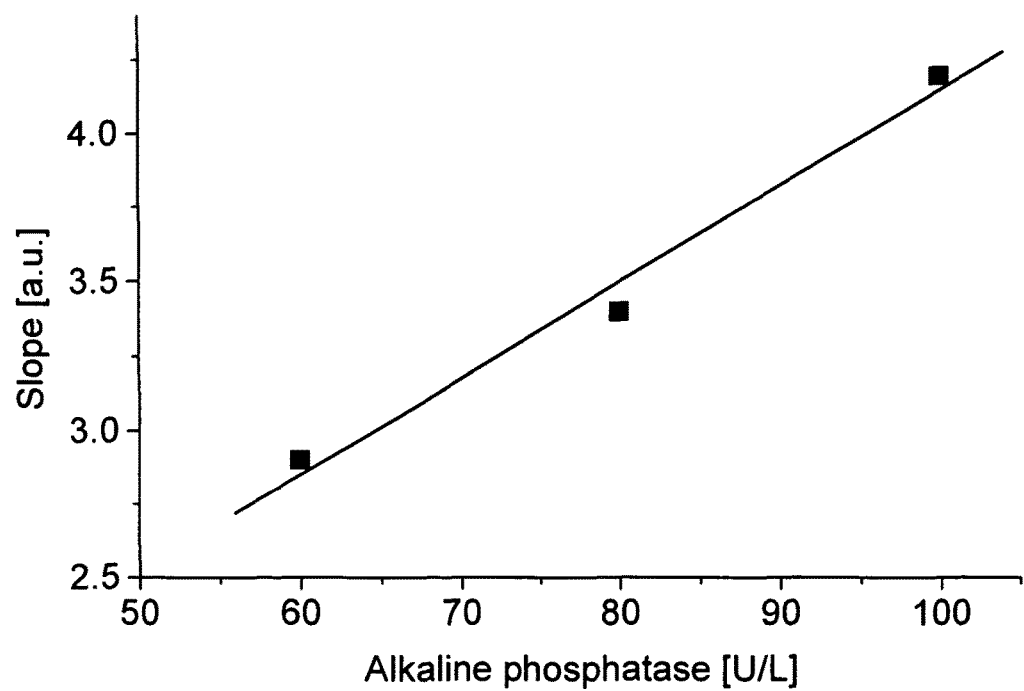
FIG. 6 shows a standard curve of an alkaline phosphate assay.

FIG. 6 shows a standard curve of an assay method for alkaline phosphatase. The ordinate (slope) has been calculated from the change of fluorescence intensity as function of time, and it corresponds to enzyme activity of the sample.

Figure shows standard curve for creatinine. Intersect of the standard curve and the line for 3SD of the negative control samples (horizontal dashed line) gives detection limit for the assays method.

EXAMPLES

The invention is illustrated by Examples 1-15 as follows, however, the applications where this invention has been proven to provide advantages are not limited to these examples.

Example 1

Interference of Hemolysis on Signal Intensity of One-Photon Excited Fluorescence and Two-Photon Excited Fluorescence Bovine serum albumin (BSA) was labeled with a fluorescent labeling reagent, ArcDia BF560 (Arctic Diagnostic Oy, Turku, Finland) to give label-BSA conjugate with substitution degree of 2.7. The conjugate was diluted with hemoglobin solution (variable concentration of hemoglobin, TRIS 50 mM, NaCl 150 mM, NaN3 10 mM, Tween 20 0.01%, BSA 0.5%, pH 8.0) to concentration of 100 nM. This solution was dispensed in the wells of a microtitration plate of either 384-well format (Greiner BIO-One GmbH, Code: 788096, pClear SV-plate, 2nd Gen, with black walls and plastic foil bottom) or 96-well format (Greiner BIO-One GmbH, code 655096) in aliquots of 10 and 100 µl, respectively. The 96-well plate was measured with a conventional one-photon excitation fluorometer (Ascent, Thermo Electron Oy, Vantaa, Finland) using excitation filter of 530 nm and emission filter 590 nm. The 384-well plate was measured with ArcDia™ TPX Plate Reader (Arctic Diagnostics Oy, Turku, Finland), a prototype microfluorometer specially designed for measurement of fluorescence from the surface of individual microparticles according to the ArcDia TPX bioaffinity assays principle [Hänninen et al., Nat. Biotechnol. 18 (2000) 548]. The instrument used in this study is a modification of the system that was recently described in detail by Soini et. al. (Rev. Sci. Instr. 2002, 37, 7, 2680). The Plate Reader is capable of measuring samples in standard microtitration plates. It is equipped with an autofocus function, to accurately position the laser beam focus within the sample in a well of a microtitration plate, and a long working distance objective to facilitate reading from microwells of different bottom thickness. The scheme of the optical configuration of the instrument is shown in FIG. 1. A passively Q-switched, diode pumped, micro-chip Nd:YAG laser LASER (NanoPulse NP-07014-400, Nanolase, Meylan France) is used as a light source for two-photon fluorescence excitation. The laser generates nanosecond pulses at 1064 nm with 17 kHz repetition rate. The incident laser light is focused through the bottom of the microwell plate, into the sample, using microscope objective Lens (Lens, Leica C-Plan 63x/0.75, Leica Microsystems, Bensheim, Germany). The average optical laser power of the focused laser beam is ~40 mW. The two-photon excited fluorescence signal is directed through the dichroic mirror DM1 and filtered by dichroic mirror DM2 and a band pass filter F1 and recorded by the photomultiplier tube CPM1 in the wavelength range of 535-600 nm. The fluorescence signals of three replicate samples were averaged and normalized, and are presented as function of hemoglobin concentration in FIG. 2. The figure shows a dramatic interference of hemoglobin on the signal of one-photon excited fluorescence whereas in case of two-photon excited fluorescence only a weak interference is seen. This result suggests that TPE detection technique provides remarkably better assay accuracy than techniques based on one-photon fluorescence detection.

Example 2

Effect of Cuvette Material on Inter-Cuvette Precision

Mouse monoclonal antibody was labeled with fluorescent label ArcDia BF 560-SE (Arctic Diagnostics Oy, Turku, Finland) according to a standard protocol [M. E. Waris et al. Anal. Biochem. 309 (2002), 67-74] to give a conjugate with substitution degree of 3.2 labels per IgG. The conjugate was diluted with buffer (TRIS 50, NaCl 150 mM, NaN$_3$ 10 mM, BSA 0.5%, Tween 20 0.01%, pH, 8.0) to concentration of 50 nM and dispensed into wells of two different microplates of 384-well format. One of the microplates was a low-cost standard microplate with plastic foil bottom window (Greiner BIO-One GmbH, Code: 788096, pClear SV-plate, 2nd Gen, with black walls and plastic foil bottom) while the other was a special plate with bottom window made of the highest quality optical glass (Greiner, SensoPlate™ 96 Well). The samples were measured with the two-photon excitation microfluorometer (ArcDia TPX Plate Reader, described in Example 1) in eight sample replicates using integration time of 10 seconds per well. Inter-cuvette variation was calculated in units of coefficient of variation. The results show (Table 1) that the two different plates provide comparable inter-cuvette measurement precision.

TABLE 1

Precision of TPE measurement using (i) cuvettes of highest quality optical glass (ii) and cuvettes with optical wall of plastic foil

| Plate of plastic foil | | | Plate of optical glass | | |
| --- | --- | --- | --- | --- | --- |
| Cuvette # | Signal | CV (%) | Cuvette # | Signal | CV (%) |
| 1 | 63.0 | 0.95 | 1 | 66.1 | 0.81 |
| 2 | 64.0 | | 2 | 67.2 | |
| 3 | 63.3 | | 3 | 67.5 | |
| 4 | 64.4 | | 4 | 66.8 | |
| 5 | 63.2 | | 5 | 66.8 | |
| 6 | 64.7 | | 6 | 67.2 | |
| 7 | 63.8 | | 7 | 67.0 | |
| 8 | 63.6 | | 8 | 66.0 | |

Example 3

Assay of Total Bilirubin

The assay for total bilirubin was performed according to a modification of the assay protocol for total bilirubin of Sigma Diagnostics® (procedure no 605), which is based on the reaction between bilirubin and diazonium salts. The assay procedure no. 605 was followed with an exception that the addition of the alkaline tartrate reagent was omitted. Bilirubin was dissolved in a mixture containing 1 part dimethyl sulfoxide and 2 parts sodium carbonate (100 mM, aq.), and diluted further with buffer (Bovine serum albumin 40 g/l, TRIS 100 mM, pH 7.4) to give bilirubin standards of 2, 5, 10, 15 and 20 mg/dl. 2 µl of a bilirubin standard sample was dispensed in a assay cuvette (384-well plate, Greiner BIO-ONE GmbH, Code: 788096), followed by addition of caffeine solution (10 µl, caffeine 25 WI, sodium benzoate 38 WI, in NaAc solution, code 605-2, Sigma) and diazo reagent solution (5 µl, sulfanilic acid 1.25 mM, $NaNO_2$ 1 mM, HCl 0.05 M). The mixture was stirred properly followed by addition of cysteine reagent (1 µl, code 605-6, Sigma, reconstituted with 10.5 ml of $H_2O$). The reaction mixture was incubated for 3 min at room temperature. Fluorescence emission from the samples was collected in the range of 630-660 nm with two-photon excitation microfluorometer (ArcDia TPX Plate Reader, described in Example 1) using integration time of 10 seconds. The fluorescence signal is presented as function bilirubin standard in FIGS. 3 and 4 (i.e. standard curve).

Example 4

Assay of Glucose

The fluorometric assay of glucose is based on two consecutive enzymatic reactions. First, glucose is oxidized by molecular oxygen in the presence of glucose oxidase. As result of the reaction, gluconolactone and hydrogen peroxide are formed. In the following second step, fluorogenic reagent, Amplex Red™, is oxidized by hydrogen peroxide in the presence of horseradish peroxidase enzyme (HRP) to yield fluorescent product "resorufin". The reaction procedure is as follows: Glucose standard stock solution was prepared by dissolving 0.198 g of D-(+)-glucose monohydrate in 10 ml assay buffer ($NaH_2PO_4$ 10 mM, NaCl 150 mM, pH 6.2). The stock solution was then diluted with the buffer to give glucose standards of variable concentrations. Assay reagent cocktail was prepared by mixing, in equivolume ratios, glucose oxidase (6 U/ml, Sigma G-7016), HRP (300 mU/ml, Sigma P8375) and Amplex Red (75 PM, Molecular Probes A-12222). The reagent cocktail was used without delay. The assay reagent cocktail (75 µl) was dispensed in assay wells (96-well plate by Greiner BIO-One GmbH, cat no GRE 655096) followed by addition of a standard sample (75 µl). The assay was incubated for a variable time (15 min, 30 min and 1 h) at 32° C., and then measured in timed fashion with two-photon excitation microfluorometer (ArcDia TPX Plate Reader, described in Example 1) using integration time of 10 seconds. The signal response and inter-cuvette precision of the assay is presented in FIG. 5 and Table 2, respectively.

TABLE 2

Inter-cuvette precision of the glucose assay

| Glucose (µM) | Incubation time | | |
|---|---|---|---|
| | 15 min | 30 min | 1 h |
| 1 | 4% | 4% | 2% |
| 3 | 3% | 3% | 3% |
| 10 | 2% | 1% | 1% |
| 30 | 1% | 1% | 0.02% |
| 100 | 1% | | |

Example 5

Assay of Amylase

For the assay of amylase, α-1,4-oligosaccharide was labeled with a fluorophore and a quencher to the reducing end and to the non-reducing end, respectively. The resulting conjugate exhibits reduced fluorescence emission compared to the emission of free fluorophore, due to proximity quenching by the quencher moiety. The conjugate works as a substrate for amylase enzyme and can thus be used for determination of activity of amylase in clinical chemistry samples. In the presence of amylase, the oligosaccharide conjugate is digested. The fluorophore and the quencher are hereby split apart leading to less efficient quenching and increase in detected fluorescence emission.

Example 6

Assay of Alkaline Phosphatase

The assay for alkaline phosphatase (ALP, EC 3.1.3.1) can be performed using a fluorogenic substrate which upon hydrolysis by the enzyme alkaline phosphatase results in increase in fluorescence. The increase in fluorescence as a function of time (=slope) is proportional to the activity of the analyte. In this example the assay was performed using DDAO-phosphate (Molecular Probes, D-6487) as a fluorogenic substrate. The assay was performed as follows: The ALP stock solution was prepared by dissolving 0.54 mg of lyophilised alkaline phosphatase (P-5931, Sigma, 42 U/mg) in 0.54 ml of water. The ALP stock solution was further diluted with 1.0 mM $MgCl_2$ to give ALP standard solutions with variable concentrations. The DDAO-phosphate stock solution was prepared by dissolving 1.11 mg of DDAO-phosphate in 0.525 ml of N,N-dimethylformamide. The assay reagent was prepared by diluting 66 µl of the DDAO-phosphate stock solution with 7.36 ml of glycine buffer (100 mM glycine, 1.0 mM $MgCl_2$, 1.0 mM $ZnCl_2$, pH 10.4). The assay reagent (75 µl) was dispensed in assay wells (96-well plate by Greiner BIO-One GmbH cat no GRE-655096) followed by addition of ALP standard sample (7.5 µl). The assay was incubated at 32° C. and measured kinetically with two-photon excitation microfluorometer (ArcDia TPX Plate Reader) in 5 min intervals using integration time of 15 sec. From the kinetic data, increase of fluorescence intensity as function of time (=slope) for each standard sample was calculated and the results are presented in FIG. 6.

Example 7

Assay of Creatinine

This assay method for creatinine is based on the use of five different enzymes and two step assay protocol. In the first step creatine is metabolized by three consecutive enzyme catalysed reactions (creatinase, sarcosine oxidase, catalase). Removal of creatine is followed by the second step, where creatinine is assayed by means of four consecutive enzyme catalysed reactions (creatininase, creatinase, sarcosine oxidase, and horseradish peroxidase). The reaction path yields the fluorescent end product "resorufin".

Figure 7:
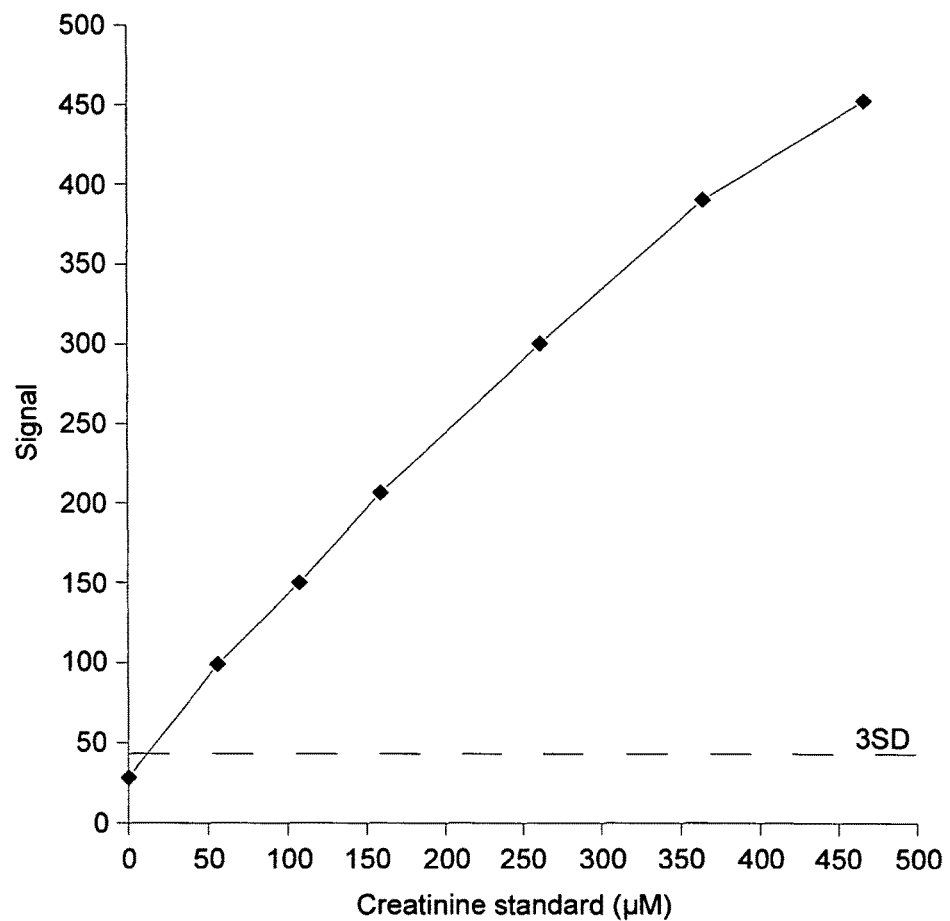
FIG. 7 shows a standard curve of a creatinine assay.

Creatinine standard (10 microliter, in buffer containing 10 mM $NaH_2PO_4$, 150 mM NaCl, titrated to pH 8) was dispensed in the assay wells (384-well plate from Greiner BIO-ONE, cat no GRE 7810966) followed by addition of 5 µl of Assay Reagent 1 (containing sarcosine oxidase 80 KA creatinase 140 kU/l, horseradish peroxidase 20 kU/l, catalase solution 200 kU/l). The assay was incubated at room temperature in the dark for 45 min. 5 µl of Assay Reagent 2 (containing creatininase 60 KA Amplex Red 300 µM) was dispensed in the assay wells. The assay was incubated for 15 min, followed by measurement with ArcDia TPX Plate Reader (Koskinen J. O. et al., 2004, Anal Biochem 328, 210-218) using the solution measurement mode and integration time of 10 sec. The results are presented in FIG. 7.

Example 8

Assay of Creatine Kinase

Creatine kinase catalyses the reaction between creatine phosphate and ADP to yield creatine and ATP. The assay method for creatine kinase is based on determination of hydrogen peroxide after conversion of creatine with the aid of creatinase and sarcosine oxidase. The reaction sequence results in liberation of hydrogen peroxide, which is measured by the standard method using fluorogenic "Amplex Red" substrate and horseradish peroxidase as catalyst.

Example 9

Assay of Alanine Aminotransferase (ALAT)

The assay method for alanine aminotransferase is based on determination of pyruvate after conversion of L-alanine and 2-oxoglutarate to pyruvate and L-glutamate. Pyruvate is further reacted with phosphate by pyruvate oxidase catalysis to yield acetylphosphate, hydrogen peroxide and carbondioxide. Hydrogen peroxide is finally measured with a standard method using fluorogenic "Amplex Red" substrate and horseradish peroxidase as catalyst.

Example 10

Assay of Aspartate Aminotransferase (ASAT)

Aspartate aminotransferase catalyses conversion of L-aspartate and 2-oxoglutarate to oxaloacetate and L-glutamate. Oxaloacetate is further converted to pyruvate with the aid of oxaloacetate decarboxylate. Pyruvate is further reacted with phosphate by pyruvate oxidase catalysis to yield acetylphosphate, hydrogen peroxide and carbondioxide. Hydrogen peroxide is finally measured with a standard method using fluorogenic "Amplex Red" substrate and horseradish peroxidase as catalyst.

Example 11

Assay of Calcium

Calcium is measured by means of calcium specific chelating agents, which is characterized with increase in fluorescence efficiency or change in the emission wavelength upon complex formation with calcium ions.

Example 12

Assay of Total Cholesterol

Cholesterol esters of the sample are first converted to cholesterol and fatty acids with the aid of cholesterol esterase. Cholesterol is then converted to cholest-4-ene-3-one by cholesterol oxidase catalysis. This conversion is accompanied with liberation of hydrogen peroxide, which is measured by the standard method using fluorogenic "Amplex Red" reagent as substrate, horseradish peroxidase as catalyst and detection with a two-photon excitation fluorometer.

Example 13

Assay of HDL Cholesterol

Lipoprotein fractions other than HDL fraction are blocked with by addition of blocking agents ($\alpha$-cyclodextrin and $Mg^{2+}$). HDL fraction of cholesterol is converted to cholest-4-ene-3-one with aid cholesterol oxidase enzyme with increased specificity to HDL cholesterol. This conversion is accompanied with liberation of hydrogen peroxide, which is measured by the standard method using fluorogenic "Amplex Red" reagent as substrate, horseradish peroxidase as catalyst and detection with a two-photon excitation fluorometer.

Example 14

Assay of Triglycerides

Triglycerides are hydrolyzed by the aid of lipase to give fatty acids and glycerol. Glycerol is then phosphorylated by treatment of ATP and glycerol kinase to produce glycerol-3-phosphate and ADP. Glycerol-3-phosphate is finally oxidased by $O_2$ with the aid of glycerolphosphate oxidase to produce dihydroxyacetone phosphate and hydrogen peroxide. Hydrogen peroxide is measured by the standard method using fluorogenic "Amplex Red" reagent as substrate, horseradish peroxidase as catalyst and detection with a two-photon excitation fluorometer.

The invention claimed is:
1. An in vitro diagnostic method comprising quantification of a clinical chemistry analyte from a clinical sample wherein the clinical chemistry analyte
   a) undergoes a chemical reaction or reactions with a reagent or reagents in one or several steps, or in a reaction sequence, or
   b) catalyzes a chemical reaction, or reactions, or a reaction in a reaction sequence of a reagent or reagents, in one or several steps;
   in a reaction system, said reaction or reactions or reaction sequence resulting in a change of a measurable property of a compound or compounds of said reaction or reactions or reaction sequence wherein
   i) said chemical reaction or reactions or reaction sequence results in
      formation of a two-photon fluorescent compound, or
         a change in two-photon fluorescence properties of the reaction system comprising at least one two-photon fluorescent compound; and ii) said analyte is quantified by exciting said two-photon fluorescent compound or compounds, measuring simultaneous two-photon excited fluorescence, and relating said measured fluorescence to method standardization data based on measurements obtained from reference material of said analyte and wherein said method comprises the steps of
a) bringing the clinical sample comprising the clinical chemistry analyte into contact with a specific assay reagent or reagents;
b) allowing, in the reaction system, said analyte to undergo a chemical reaction with said reagent or reagents, or allowing said analyte to catalyze a chemical reaction or reactions of said reagent or reagents;
c) optionally repeating steps a) and b) one or several times;
d) said reaction or reactions of step or steps b) resulting in formation of a two-photon Fluorescent compound, or resulting in a change in two-photon fluorescence properties of said reaction system comprising at least one two-photon fluorescent compound; and
e) quantifying said analyte by exciting said two-photon fluorescent compound or compounds, measuring simultaneous two-photon excited fluorescence, and relating said measured fluorescence to method standardization data based on measurements obtained from reference material of said analyte,
wherein said two-photon fluorescent compound is contained in a non-spectrophotometric quality cuvette.

2. The method according to claim 1, wherein fluorescence resulting from two-photon fluorescence excitation is measured kinetically.

3. The method according to claim 1, wherein fluorescence resulting from two-photon fluorescence excitation is measured as an end-point signal.

4. The method according to claim 1, wherein quantification of the clinical chemistry analyte is carried out for several samples by repeating the steps a) to e) for each sample.

5. The method according to claim 1, wherein several clinical chemistry analytes are quantified by repeating the steps a) to e) for each analyte.

6. The method according to claim 1, wherein the clinical chemistry analyte or analytes are selected from the group consisting of albumin, total protein, hemoglobin, ammonia, carbonate, bilirubin direct, bilirubin total, calcium, chloride, iron, magnesium, phosphate, cholesterol HDL, cholesterol LDL, cholesterol total, creatinine, fructosamine, glucose, lactate, triglycerides, urea, uric acid, acid phosphatase, alkaline phosphatase, alanine aminotransferase, aspartate aminotransferase, amylase pancreatic, amylase total, cholin esterase, creatine kinase, glutamyl transferase, glutamate dehydrogenase, hydroxybutyrate dehydrogenase, lactate dehydrogenase and lipase.

7. The method according to claim 1, wherein said cuvette comprises a microtiter plate.

* * * * *

UNITED STATES PATENT AND TRADEMARK OFFICE
CERTIFICATE OF CORRECTION

PATENT NO. : 10,295,465 B2
APPLICATION NO. : 10/588861
DATED : May 21, 2019
INVENTOR(S) : Erkki Soini et al.

It is certified that error appears in the above-identified patent and that said Letters Patent is hereby corrected as shown below:

On the Title Page

Item (75), Line 1, correct the spelling of the second inventor's first name from "Aloksi" to --Aleksi--.

Signed and Sealed this
Thirtieth Day of July, 2019

Andrei Iancu
*Director of the United States Patent and Trademark Office*

UNITED STATES PATENT AND TRADEMARK OFFICE
CERTIFICATE OF CORRECTION

| | | |
|---|---|---|
| PATENT NO. | : 10,295,465 B2 | Page 1 of 1 |
| APPLICATION NO. | : 10/588861 | |
| DATED | : May 21, 2019 | |
| INVENTOR(S) | : Erkki Soini et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2935 days.

Signed and Sealed this
Seventh Day of July, 2020

Andrei Iancu
*Director of the United States Patent and Trademark Office*